United States Patent

Wentler

[11] 4,000,091
[45] Dec. 28, 1976

[54] BUILT DETERGENT COMPOSITIONS

[75] Inventor: George Edward Wentler, West Chester, Ohio

[73] Assignee: The Procter & Gamble Company, Cincinnati, Ohio

[22] Filed: Apr. 2, 1975

[21] Appl. No.: 562,310

[52] U.S. Cl. .............. 252/524; 252/526; 252/542; 252/545; 252/546; 260/501.12

[51] Int. Cl.² .............. C11D 3/066; C11D 1/18

[58] Field of Search ............ 252/542, DIG. 1, 524, 252/547, 545, 526; 8/137; 260/501.12, 458

[56] References Cited

UNITED STATES PATENTS

| | | | |
|---|---|---|---|
| 2,781,390 | 2/1957 | Mannheimer | 260/458 |
| 3,280,179 | 10/1968 | Ernst | 260/501.12 |
| 3,359,275 | 12/1967 | Mannheimer | 252/542 X |
| 3,424,545 | 1/1969 | Bauman | 252/89 |
| 3,449,430 | 6/1969 | Dohr et al. | 252/547 X |
| 3,452,066 | 6/1969 | Mannheimer | 252/550 X |
| 3,503,890 | 3/1970 | Davission et al. | 252/547 X |
| 3,505,396 | 4/1970 | Sanders et al. | 252/545 X |
| 3,619,115 | 11/1971 | Diehl et al. | 8/137 |
| 3,668,240 | 6/1972 | Barbera | 260/501.12 |
| 3,684,427 | 8/1972 | Walz et al. | 8/26 |
| 3,769,311 | 10/1973 | Armstrong et al. | 252/545 X |
| 3,813,349 | 5/1974 | Wolfson | 252/526 |
| 3,925,262 | 12/1975 | Laughlin et al. | 252/545 |
| 3,929,678 | 12/1975 | Laughlin et al. | 252/526 |

*Primary Examiner*—Thomas J. Herbert, Jr.
*Attorney, Agent, or Firm*—Charles R. Wilson; Jerry J. Yetter; Richard C. Witte

[57] ABSTRACT

Detergent compositions comprising builders and zwitterionic surfactants of the formula

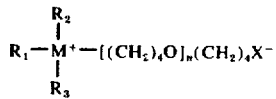

wherein $R_1$, $R_2$ and $R_3$ are hydrocarbon groups, $n$ is 1 to 20, M is nitrogen or phosphorus, and X is, for example, sulfate or sulfonate.

20 Claims, No Drawings

BUILT DETERGENT COMPOSITIONS

BACKGROUND OF THE INVENTION

This invention relates to built detergent compositions containing tetramethylene oxide (TMO) surfactants. More particularly, this invention encompasses built detergent compositions comprising, as the surfactant, novel zwitterionic compounds characterized by a particular placement and number of TMO groups and particular hydrophobic groups. Importantly, the TMO moiety can be introduced into the instant surfactant compounds using tetrahydrofuran as a precursor. Tetrahydrofuran, in turn, is available from plant by-products such as corncobs, oat hulls, cottonseed hulls, and bagasse. To this extent, the zwitterionic surfactants used herein are not based on scarce petro-chemical feedstocks in the manner of ethylene oxide-containing detersive surfactants.

The use of zwitterionic compounds (i.e., the so-called "internally neutralized" surface active compounds having both positive and negative charge centers) in laundry detergents is known. In contrast with many prior art zwitterionic detersive surfactants, the compositions herein employ zwitterionic compounds having a TMO substituent which provides both charge separation and hydration interposed between the oppositely-charged centers of the molecule. The TMO-zwitterionics are particularly useful for removing clay and oily soils from fabrics, even in low- or non-built detergent compositions. Moreover, the use of builders in combination with the TMO-zwitterionics in the manner of the present invention allows the formulation of superior detergents at a more economical cost.

PRIOR ART

Various zwitterionic compounds have been suggested for use in both built and builder-free detergent compositions.

U.S. Pat. No. 3,684,427, to Walz, et al., issued Aug. 15, 1972, discloses alkoxylated zwitterionic surfactants and their use in fabric dyeing operations.

Belgian Pat. No. 813,502 to GAF Corporation, relates to di-ethoxylated quaternary ammonium compounds, phosphated or sulfated to form amphoteric surfactants. The compounds contain two alkylene oxide chains. U.S. Pat. No. 3,505,396, to H. L. Sanders, et al., issued Apr. 7, 1970, relates to sulfopropylated amphoteric surfactants containing ethylene oxide chains. U.S. Pat. No. 3,673,158, to A. M. Reader, et al., issued June 27, 1972, relates to sulfobetaine glycol modified with poly(ethylene terephthalate). U.S. Pat. No. 3,239,560, to C. M. Cambre, et al., issued Mar. 8, 1966, relates to the preparation of sulfobetaines having a hydroxy-substituted alkylene moiety interposed between the positive and negative charge centers of the surfactant-type molecules. U.S. Pat. No. 2,185,163, to H. Ulrich, issued Dec. 26, 1939, relates to alkoxylated derivatives of amine oxides containing anionic substituents. U.S. Pat. No. 2,115,250, to H. A. Bruson, issued Apr. 26, 1938, relates to alkoxylated amines and their salts and to the quaternary ammonium bases and salts derived from said amines. British patent specification No. 465,200, complete specification accepted Apr. 26, 1937, relates to quaternary ammonium or phosphonium, or tertiary sulfonium, compounds containing ether or polyether groups.

The co-pending application of Laughlin, Gosselink, Cilley, and Heuring, Ser. No. 493,951, filed Aug. 1, 1974, now U.S. Pat. No. 3,929,678 relates to zwitterionic surfactants having ethylene oxide moieties interposed between the cationic and anionic charge centers. The co-pending application of Laughlin, Gosselink, and Cilley, Ser. No. 493,956, filed Aug. 1, 1974, now abandoned relates to di-ethoxylated zwitterionic compounds having ethylene oxide groups interposed between the charge centers.

U.S. Pat. Nos. 3,668,240, issued June 5, 1972 and 3,764,568, issued Oct. 9, 1973, both to Barbera, disclose zwitterionic detergents having a 1,4-(2-butenylene) moiety between charge centers. See also U.S. Pat. No. 3,619,115, issued Nov. 9, 1971, to Diehl and Smith, which discloses zwitterionics in combination with builders and electrolytes. U.S. Pat. Nos. 3,452,066, issued June 24, 1969, and 2,781,390, issued Feb. 12, 1957, both to Mannheimer, broadly relate to various zwitterionic surfactants optionally containing a seemingly limitless variety of oxygen-containing, presumably hydrophilic, moieties, including alkylene oxides. U.S. Pat. No. 3,769,311, issued Oct. 30, 1973, to Armstrong and Dawald, discloses ethoxylated ammonio carboxylate zwitterionics, and describes compounds having limited ranges of ethyleneoxy and hydrophobic groups attached to the positive charge center. Also, Belgium Arrete No. 806,567 issued Oct. 29, 1973 to Recket and Colman Products, Ltd., discloses anionic ethoxylated amino sulfonates. (See also Japanese 3555 (1962), to Komori and Kashiwabara, Chem. Abstracts 53:4756e; British Pat. No. 1,296,351, complete specification published Nov. 15, 1972, to Cheng et al.; U.S. Pat. No. 3,178,366, issued Apr. 13, 1965, to Du Brow and Brandiff; U.S. Pat. No. 2,940,816, issued June 14, 1960, to Sniegowski; and German application No. 1,159,957, filed Nov. 8, 1970 by Glabisch, et al., for other zwitterionic and/or quaternary ammonium compounds.)

The co-pending applications of Laughlin, et al., and Laughlin, et al., Ser. Nos. 493,952 and 493,953, each filed Aug. 1, 1974, now U.S. Pat. Nos. 3,925,262 and 3,929,678 relate to the use of ethoxylated zwitterionics with builders and/or auxiliary surfactants. The concurrently-filed application of Gosselink, et al., entitled DETERGENT COMPOUNDS, Ser. No. 562,307, filed Apr. 2, 1976, the disclosures of which are incorporated herein by reference, describes the TMO-based zwitterionic surfactants used in the instant compositions.

SUMMARY OF THE INVENTION

This invention encompasses detergent compositions, comprising:

a. a detersive amount (i.e., from about 1% to about 99%, preferably 6% to 50%, by weight) of a water-soluble surfactant of the formula

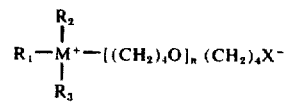

wherein $R_1$, $R_2$, $R_3$, M, X and $n$ are as defined below; and b. an effective amount (i.e., from about 5% to about 95%, preferably 15% to 65%, by weight) of a detergency builder.

The balance of the compositions can comprise various detergency adjuncts, fillers, carriers, and the like, well-known in the detergency arts.

DETAILED DESCRIPTION OF THE INVENTION

The detergent compositions of this invention comprise a zwitterionic surfactant and a detergency builder, which are described, in turn, below.

SURFACTANT

The detersive zwitterionic surfactants used herein are molecules which can be visualized as being made up of four distinct parts. Referring to the foregoing formula, the compounds herein comprise a hydrocarbon portion composed of groups $R_1$, $R_2$ and $R_3$, a cationic charge center, M, an anionic charge center, X, and a tetramethylene oxide moiety interposed between said cationic and anionic charge centers.

The hydrocarbon portion of the zwitterionic surfactants can comprise straight chain, branched chain, etc., alkyl or alkenyl moieties, or aryl or alkaryl moieties, all as more fully described hereinafter. It will be understood by those skilled in the detergency arts that the hydrocarbon groups $R_1$, $R_2$ and $R_3$ can contain other substituents, such as halogen, hydroxyl, alkoxyl, and the like.

The cationic charge center in the detersive zwitterionics is ammonium or phosphonium, with ammonium being preferred due to the availability of amine precursor compounds and the desirability of providing phosphorus-free compositions.

The anionic charge center, X, can be, for example, sulfonate, sulfate, phosphonate, and like negatively charged moieties well recognized in the detergency arts as useful for imparting water solubility to detersive surfactants. Compounds of the present type wherein X is sulfate or sulfonate are highly preferred from the standpoint of ease-of-manufacture and detergency performance.

The present compounds are characterized by one or more TMO moieties interposed between the cationic and anionic charge centers of the molecule. The degree of polymerization of the TMO moieties is designated in the formula by integer $n$, which, in general, is within the range from about 1 to about 20, preferably from about 1 to about 10.

More particularly, hydrocarbon groups $R_1$, $R_2$ and $R_3$ can be independently selected from $C_1$–$C_{30}$ alkyl or alkenyl moieties; aryl moieties, such as phenyl, naphthyl, and the like; alkaryl moieties having an alkyl group in the range of $C_1$ to about $C_{30}$; or two R groups can be joined to form a $C_4$–$C_6$ heteroring compound with M.

When selecting a detersive surfactant of the present type, it will be recognized that groups $R_1$, $R_2$ and $R_3$ should preferably be selected to provide sufficient hydrocarbon content that the hydrocarbon portion of the molecule has substantial hydrophobic character. (However, even those zwitterionics wherein the R groups are all relatively short-chain, i.e., $C_1$–$C_4$, do provide a useful level of light-duty cleaning.) More particularly, groups $R_1 + R_2 + R_3$, together, preferably contain at least about 12 carbon atoms, more preferably at least about 14 carbon atoms.

Based on the foregoing considerations regarding the total hydrocarbon content of the groups $R_1 + R_2 + R_3$, it will be recognized by those skilled in the detergency arts that the hydrophobic character for superior detergency performance is secured when, for example, group $R_1$ is a straight chain or branched chain $C_{10}$–$C_{30}$ alkyl or alkenyl moiety, or an alkaryl moiety having a $C_6$–$C_{24}$ alkyl group, and $R_2$ and $R_3$ are each independently selected from $C_1$–$C_4$ alkyl or alkenyl moieties. Compounds wherein groups $R_1$ and $R_2$ are each independently selected from $C_6$–$C_{21}$ alkyl or alkenyl moieties and alkaryl moieties having a $C_6$–$C_{15}$ alkyl group, and wherein $R_3$ is a $C_1$–$C_4$ alkyl or alkenyl moiety, also have sufficient hydrocarbon content that the molecule has substantial hydrophobic character, and these are also highly useful detersive surfactants. Compounds wherein $R_1$, $R_2$ and $R_3$ are each independently selected from $C_6$–$C_{16}$ alkyl or alkenyl moieties and alkaryl moieties having a $C_6$–$C_{10}$ alkyl group are also useful detersive surfactants.

Typical detersive surfactants herein include the zwitterionic compounds wherein $R_1$ is a straight chain or a branched chain $C_{10}$–$C_{30}$ alkyl or alkenyl moiety, or an alkaryl moiety having a $C_6$–$C_{24}$ alkyl group (preferably $R_1$ is a $C_{14}$–$C_{22}$ alkyl moiety or alkaryl moiety having a $C_8$–$C_{16}$ alkyl group; more preferably $R_1$ is a $C_{14}$–$C_{20}$ alkyl moiety); $R_2$ and $R_3$ are each independently selected from $C_1$–$C_4$ alkyl or alkenyl moieties or hydroxy-substituted $C_1$–$C_4$ alkyl or alkenyl moieties (preferably $R_2$ and $R_3$ are each independently selected from $C_1$–$C_3$ alkyl moieties, especially methyl); X is sulfate or sulfonate; and $n$ is an integer of at least 1 (preferably $n$ is an integer from about 1 to about 10).

Other detersive surfactants are those wherein $R_1$ and $R_2$ are each independently selected from $C_6$–$C_{22}$ alkyl or alkenyl moieties and alkaryl moieties having a $C_6$–$C_{16}$ alkyl group (preferably $R_1$ and $R_2$ are each independently selected from $C_8$–$C_{16}$ alkyl moieties, most preferably $C_{10}$–$C_{14}$ alkyl moieties); $R_3$ is a $C_1$–$C_4$ alkyl or alkenyl, or $C_1$–$C_4$ hydroxy-substituted alkyl or alkenyl moiety (preferably $R_3$ is $C_1$–$C_3$ alkyl, especially methyl) the sum of $R_1 + R_2 + R_3$ carbon atoms being in the range from about 13 to about 50 (preferably in the range from about 14 to about 40); and wherein X and integer, $n$, are as defined immediately hereinabove.

Other representative detersive surfactants of the present type are those wherein groups $R_1$, $R_2$ and $R_3$ are each independently selected from $C_6$–$C_{16}$ alkyl or alkenyl moieties and alkaryl moieties having a $C_6$–$C_{10}$ alkyl group (preferably $R_1$, $R_2$ and $R_3$ are each independently selected from $C_8$–$C_{16}$ alkyl moieties, more preferably $C_8$–$C_{12}$ alkyl) the sum of $R_1 + R_2 + R_3$ carbon atoms being in the range from about 18 to about 48 (preferably about 24 to about 36); and wherein X and integer, $n$, are as defined immediately hereinabove.

The synthesis of the zwitterionic compounds used herein is carried out using commercially available starting materials. A non-limiting example of one such general synthetic route is as follows.

According to procedures described in the literature, tetrahydrofuran is refluxed with thionyl chloride and sulfuric acid for ca. 72 hours to provide a polymeric TMO-based dichloride. Sodium hydride is reacted with 1,4-tetramethylene glycol (excess, as solvent) until hydrogen evolution ceases and then reacted with the above dichloride to provide the corresponding poly-TMO glycol. The glycol is thereafter tosylated in standard fashion with tosyl chloride to form the corresponding TMO ditosylate. The ditosylate is then reacted with a tetiary amine (or phosphine) to form the TMO-based amine tosylate. The amine tosylate is thereafter reacted with sodium sulfite to form the TMO-based zwitterionic sulfonate, which is purified on a mixed bed (H⁺, OH⁻ form) resin.

It will be appreciated that zwitterionic compounds of the general formula above can be prepared using any of a variety of tertiary amines or phosphines. Moreover, zwitterionic compounds having any desired degree of polymerization of the TMO moiety (*n*) can be prepared in the same general fashion.

The following illustrates the preparation of TMO-zwitterionics useful herein, but is not intended to be limiting thereof. Reaction precursors and products include, inter alia, the following, wherein the letter designation corresponds to that used in the experimental procedure.

1,9-dichloro-5-oxanonane (A)

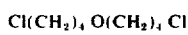

1,14-dichloro-5,10-dioxatetradecane (B)

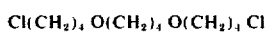

1,19-dihydroxy-5,10,15-trioxanonadecane (C)

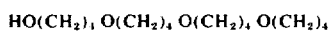

1,24-dihydroxy-5,10,15,20-tetraoxatetracosane (D)

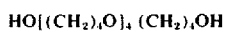

1,19-(5,10,15-trioxanonadecylene)-bis(p-toluenesulfonate) (E)

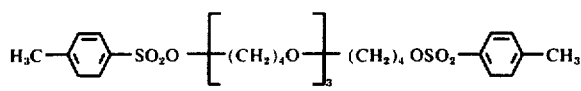

1,24-(5,10,15,20-tetraoxatetracosylene)-bis(p-toluenesulfonate) (F)

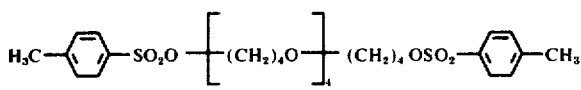

9-dimethyloctadecylammonio-5-oxanonane-1-sulfonate (G)

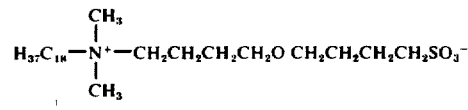

19-dimethyloctadecylammonio-5,10,15-trioxanonadecane-1-sulfonate (H)

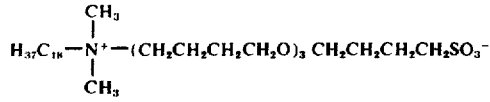

24-dimethyloctadecylammonio-5,10,15,20-tetraoxatetracosane-1-sulfonate (I)

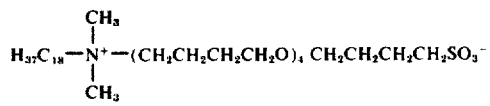

Preparation of 1,9-Dichloro-5-oxanonane (A) and 1,14-Dichloro-5,10-dioxatetradecane (B). According to the chemistry of Reppe and Mitarbeiter, Ann 596, 38(1955), 15 g. of 95% sulfuric acid and 1 Kg. (13.9 mol) of thionyl chloride were added to 1.15 Kg. (16 mol) of dry tetrahydrofuran. This mixture was heated to reflux for 72 hrs; about 650 ml. of low boiling material (< 70° C) was then distilled and the residue fractionally distilled at low pressure. The first high boiling fraction gave 524 g. (2.6 mol) of title compound (A) (72° C/0.25 torr) and the second gave 212 g. (0.78 mol) of title compound (B) (145° C/0.6 torr).

Preparation of 1,19-Dihydroxy-5,10,15-Trioxanonadecane (C). To 675 g. (7.5 mol) of 1,4-butanediol in a 3-neck, 2-l flask fitted with a mechanical stirrer, thermometer, and argon inlet valve was added 46 g. (2.0 g-atoms) of freshly cut sodium. After stirring under argon at room temperature for 16 hrs. the temperature was raised to 80° C until the sodium had been consumed and hydrogen gas evolution had ceased. Two hundred thirty grams (1.15 mol) of dichloride (A) was then added dropwise over a four-hour period under argon, with stirring, and with the temperature at 80° C. This mixture was stirred under argon at 80° C for an additional 20 hrs. and until the reaction mixture was neutral to litmus. The mixture was cooled, the precipitated sodium chloride filtered and washed with ethanol, and the filtrate distilled from solid potassium carbonate that was added to the distillation pot. After removal of low boiling material, four fractions were obtained: 204 g. (2.26 mol) of 1,4-butanediol (88° C/0.6 torr), 24.6 g. (150° C/2.0 torr) of uninvestigated material, 10.6 g. (180° C/2.0 torr) of uninvestigated material, and 50.0 g. (197–230° C/2.0 torr) of title compound (C), m.p. 22° C.

Preparation of 1,24-dihydroxy-5,10,15,20-tetraoxatetracosane (D). To 575 g. (6.4 mol) of 1,4-butanediol in a 2-l, 3-neck flask fitted with a mechanical stirrer, thermometer, and argon inlet valve was added slowly 61.5 g. (1.28 mol) of hexane rinsed sodium hydride (50% in mineral oil). After hydrogen evolution had ceased, the reaction temperature was raised to 80° C and 173 g. (0.64 mol) of dichloride (B) was added dropwise. The mixture was stirred under argon at 80° C for 17 hrs. and for an additional 50 hrs. at 130° –140° C. The mixture was then cooled, the precipitated sodium chloride filtered and washed with ethanol, and the filtrate distilled at reduced pressure. After distillation of some low boiling material, 447 g. (495 mol) of 1,4-butanediol (88° C/0.6 torr) was distilled. The pot residue was crystallized from ether. Thin layer chromatography indicated an impurity was present. Continuous extraction of the liquid melt with hexanes for 3 days removed the impurity. Crystallization from a seeded ethereal solution afforded pure title compound (D), 179 g., m.p. 34.5° – 36.5° C.

Preparation of 1,19-(5,10,15-Trioxanonadecylene-bis(p-Toluenesulfonate) (E). To 61 g. (0.20 mol) of glycol (C) in 250 ml. (3.17 mol) of dry pyridine cooled to 0°–4° C was added in small portions 84 g. (0.44 mol) of tosyl chloride (i.e., p-toluene sulfonyl chloride).

Addition of tosyl chloride, with stirring, was controlled so that the reaction temperature remained below 8° C. After stirring for 3 hrs. at 5° C, the reaction mixture was poured into a slurry of 1 liter of 12 N hydrochloric acid and 3 liters of ice. This mixture was extracted with three 500 ml-portions of chloroform. The combined extracts were washed with water, saturated sodium bicarbonate solution, dried ($Na_2SO_4$), and the solvent removed to yield the title ditosylate (E), 121 g., as a viscous oil.

Preparation of 1,24-(5,10,15,20-Tetraoxatetracosylene)-bis(p-Toluenesulfonate) (F). Forty grams (0.11 mol) of glycol (D) and 45 g. (0.23 mol) of tosyl chloride in 250 ml. (3.17 mol) of dry pyridine were allowed to react as in the preparation of E above. Evaporation of the solvent from the dried extract afforded 73 g. of product ditosylate (F) as a viscous oil.

Preparation of 9-Dimethyloctadecylammonio-5-oxanonane-1-sulfonate (G). Twenty-five grams (0.126 mol) of dichloride (A) and 37 g. (0.126 mol) of distilled (b.p. 176°–179° C) dimethyloctadecylamine were heated at reflux in 150 ml of dry acetonitrile, with stirring, for 16 hrs. The solvent was then removed and the residue dissolved in 500 ml. of water. Fifty grams (0.04 mol) of sodium sulfite were added and the reaction mixture was refluxed until all dichloride (A) had been consumed as determined by thin layer chromatography. The mixture was then cooled, and extracted with three 200 ml-portions of chloroform. The combined extracts were dried ($Na_2SO_4$), the solvent evaporated, and the residue dissolved in methanol.

The above methanol solution was stirred with 400 g. of a mixed bed ion exchange resin (Rexyn 300 H-OH, commercially available from the Fisher Scientific Company) for 5 hrs. The resin was then filtered and the methanol solution concentrated to yield 19 g. of title compound (G) m.p. 114°–116°C.

The foregoing procedure is modified by replacing the $C_{18}H_{37}(CH_3)_2N$ with an equivalent amount of n-$C_{10}H_{21}(CH_3)_2N$, n-$C_{12}H_{25}(CH_3)_2N$, n-$C_{14}H_{29}(CH_3)_2N$, n-$C_{16}H_{33}(CH_3)_2N$ and n-$C_{20}H_{21}(CH_3)_2N$, respectively, and the corresponding dimethylammonio compounds wherein $R_1$ is, respectively, n-$C_{10}$; n-$C_{12}$; n-$C_{14}$; n-$C_{16}$; and n-$C_{20}$ are secured.

Preparation of 19-Dimethyloctadecylammonio-5, 10, 15-trioxanonadecane-1-sulfonate (H). To 58 g. (0.096 mol) of ditosylate (E) in 150 ml. of dry acetonitrile was added 28 g. (0.096 mol) of distilled (b.p. 176°–179° C) dimethyloctadecylamine. This mixture was heated to reflux under argon, with stirring, for 16 hrs. The solvent was then removed and the residue dissolved in 500 ml. of methanol. Thirty-six grams (0.29 mol) of sodium sulfite in 500 ml. of water were added to the methanolic solution and this mixture was heated to reflux until thin layer chromatography indicated the absence of ditosylate (E). Additional methanol was added and the insoluble salts were filtered. The solvents were removed, the residue dissolved in methanol, and the methanolic solution purified with mixed bed resin, as above. Filtration of the resin and evaporation of the solvent afforded 15 g. of the title compound (H), m.p. 24° C.

In the foregoing procedure, the dimethyloctadecylamine is replaced by an equivalent amount of dimethyldodecylphosphine, didecylmethylphosphine and trioctylphosphine, respectively. The compounds wherein $R_1$ is dodecyl and $R_2$ and $R_3$ are each methyl; and wherein $R_1$, $R_2$ and $R_3$ are each octyl, are secured, respectively.

Preparation of 24-Dimethyloctadecylammonio-5,10,15,20-tetraoxatetracosane-1-sulfonate (I). Fifty grams (0.073 mol) of ditosylate (F) and 22 g. (0.073 mol) of distilled (b.p. 176°–179° C) dimethyloctadecylamine were allowed to react as in the preparation of (H), above. After removal of the solvent, the residue was allowed to react with 27 g. (0.21 mol) of sodium sulfite in one liter of aqueous methanol (1:1,v/v) at reflux temperatures. After purification, as in the preparation of (H), above, the compound was crystallized from 1:1 ethyl acetate-chloroform and vacuum dried to yield 12 g. of the title compound (I), m.p. 61° C.

In the foregoing procedure, the dimethyloctadecylamine is replaced by an equivalent amount of dimethylbutyl amine and the corresponding sulfonate (wherein $R_1$ is butyl and $R_2$ and $R_3$ are each methyl) is secured.

In the foregoing procedure, the dimethyloctadecylamine is replaced by an equivalent amount of dicotylmethylamine and the corresponding sulfonate (wherein $R_1$ and $R_2$ are each octyl and $R_3$ is methyl) is secured.

In the foregoing procedure the dimethyloctadecylamine is replaced by an equivalent amount of $(C_{10}H_{21})_3N$ and the corresponding sulfonate (wherein $R_1$, $R_2$ and $R_3$ are each decyl) is secured.

Preparation of 19-Dimethyloctadecylammonio-5, 10, 15-Trioxanonadecane-1Sulfate. To 61 g (0.20 mol) of glycol (C) in 250 ml (3.17 mol) of dry pyridine cooled to 0.4° C is added in small portions 38 g (0.20 mol) of tosyl chloride as in the preparation of E. Purification and removal of solvent as in the preparation of E affords a mixture of C, E, and the monotosylate of C. This mixture in 150 mls. of dry acetonitrile with 0.20 mol of dimethyloctadecylamine is heated to reflux in the manner disclosed above, and the solvent stripped on a rotary evaporator.

The mixture of material prepared in the foregoing manner is dissolved in 250 mls. of dry pyridine and cooled to 0–5° C. Chlorosulfonic acid, 56 g (0.48 mol), dissolved in 250 ml of chloroform, is added dropwise to maintain the reaction temperature below 15° C. After addition of the chlorosulfonic acid, the mixture is stirred at 0° C for 1 hr., and at room temperature for an additional hour.

Following the reaction with the chlorosulfonic acid, the chloroform is vacuum-stripped. The semi-solid residue is poured into colled 50% aqueous NaOH and extracted three times with chloroform. The combined extracts are purified with mixed bed resin (Rexyn 300 H-OH) to yield the title compound.

In the foregoing procedure, the n-$C_{18}H_{37}(CH_3)_2N$ is replaced by an equivalent amount of n-$C_{10}H_{21}(CH_3)_2N$, n-$C_{12}H_{25}(CH_3)_2N$, n-$C_{14}H_{29}(CH_3)_2N$, n-$C_{16}H_{33}(CH_3)_2N$, n-$C_{16}H_{31}(CH_3)_2N$, and n-$C_{20}H_{41}(CH_3)_2N$, respectively. The corresponding dimethylammonio sulfates wherein $R_1$ is decyl, dodecyl, tetradecyl, hexadecyl, hexadecenyl and eicosyl are secured, respectively.

In the foregoing procedure, the dimethyloctadecylamine is replaced by an equivalent amount of the following phosphines, respectively: dimethyldodecylphosphine; dimethyloctadecylphosphine; tris(decyl)phosphine; tritetradecylphosphine; and didodecylmethylphosphine. The corresponding phosphonium 5,10,15-trioxanonadecane sulfates are secured in each instance.

Preparation of 24-Dimethyloctadecylammonio-5,10,15,20-Tetraoxatetracosane-1-hydrogen Phosphate. To 40 g (0.11 mol) of glycol (D) in 100 ml of dry dimethylformamide is added 62 g (0.30 mol) of thionyl bromide. This mixture is heated until the conversion of the glycol to the dibromocompound is complete, and then neutralized with base. This neutralized mixture is extracted with chloroform, the extracts dried ($Na_2SO_4$), and the solvent removed to yield the dibromoderivative of D.

The material prepared above is then heated not higher than 130° C with 21 g (0.10 mol) of isopropylphosphite as 2-bromopropane distills. After the 2-bromopropane has all distilled, the reaction pressure is reduced to about 1 torr., whereupon additional low boiling distillates are removed.

The residue from the distillation above is cooled and chromatographed on silica gel to isolate the diisopropyl bromophosphonate. This purified monoester is allowed to react with an equal mole amount of dimethyloctadecylamine in refluxing acetonitrile in the manner disclosed above, and the solvent removed. This quaternary ammonium phosphonate ester is hydrolyzed with 3-6 N hydrochloric acid to yield, after purification and solvent removal, the title compound.

Detergency Builder

The instant compositions contain a detergency builder, and all manner of detergency builders commonly taught for use in detergent compositions are useful in combination with the TMO-zwitterionics. The detergent compositions herein can contain from about 5% to about 95%, more preferably from about 15% to about 65%, by weight of said builders. Useful builders herein include any of the conventional inorganic and organic water-soluble builder salts, as well as various water-insoluble and so-called "seeded" builders.

Inorganic detergency builders useful herein include, for example, water-soluble salts of phosphates, pyrophosphates, orthophosphates, polyphosphates, silicates, carbonates, and the like. Organic builders include various water-soluble phosphonates, polyphosphonates, polyhydroxysulfonates, polyacetates, carboxylates, polycarboxylates, succinates, and the like.

Specific examples of inorganic phosphates builders include sodium and potassium tripolyphosphates, phosphates, and hexametaphosphates. The organic polyphosphonates specifically include, for example, the sodium and potassium salts of ethylene diphosphonic acid, the sodium and potassium salts of ethane 1-hydroxy-1,1-diphosphonic acid and the sodium and potassium salts of ethane-1,1,2-triphsophonic acid. Examples of these and other phosphorus builder compounds are disclosed in U.S. Pat. Nos. 3,159,581; 3,213,030; 3,422,021; 3,422,137; 3,400,176 and 3,400,148, incorporated herein by reference. Sodium tripolyphosphate is an especially preferred, water-soluble inorganic builder herein.

Non-phosphorus containing sequestrants can also be selected for use herein as detergency builder.

Specific examples of non-phosphorus, inorganic builder ingredients include water-soluble inorganic carbonate, bicarbonate, and silicate salts. The alkali metal, e.g., sodium and potassium, carbonates, bicarbonates, and silicates are particularly useful herein.

Water-soluble, organic builders are also useful herein. For example, the alkali metal, ammonium and substitued ammonium polyacetates, carboxylates, polycarboxylates and polyhydroxysulfonates are useful builders in the present compositions and processes. Specific examples of the polyacetate and polycarboxylate builder salts include sodium, potassium, lithium, ammonium and substituted ammonium salts of ethylenediaminetetraacetic acid, nitrilotriacetic acid, oxydisuccinic acid, mellitic acid, benzene polycarboxylic (i.e., penta- and tetra-) acids, and citric acid.

Highly preferred non-phosphorus builder materials (both organic and inorganic) herein include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Other highly preferred organic builders herein are the polycarboxylate builders set forth in U.S. Pat. No. 3,308,067, Diehl, incorporated herein by reference. Examples of such materials include the water-soluble salts of homo- and co-polymers of aliphatic carboxylic acids such as maleic acid, itaconic acid, mesaconic acid, fumaric acid, aconitic acid, citraconic acid and methylenemalonic acid.

Additional, preferred builders herein include the water-soluble salts, especially the sodium and potassium salts, of carboxymethyloxymalonate, carboxymethyloxysuccinate, cis-cyclohexanehexacarboxylate, cis-cyclopentanetetracarboxylate and phloroglucinol trisulfonate.

Sodium nitrilotriacetate is an especially preferred, water-soluble organic builder herein.

Another type of detergency builder material useful in the present compositions and processes comprises a water-soluble material capable of forming a water-insoluble reaction product with water hardness cations in combination with a crystallization seed which is capable of providing growth sites for said reaction product. Such "seeded builder" compositions are fully disclosed in the co-pending application of Benjamin, Ser. No. 248,546, filed Apr. 28, 1972, the disclosures of which are incorporated herein by reference.

More particularly, the seeded builders useful herein comprise a crystallization seed having a maximum particle dimension of less than 20 microns, preferably a particle diameter of from about 0.001 micron to about 5 microns, in combination with a material capable of forming a water-insoluble reaction product with free metal ions.

Many builder materials, e.g., the water-soluble carbonate salts, precipitate water hardness cations, thereby performing a builder function. Unfortunately, many of the precipitating builders used in detergent compositions do not reduce the free metal ion content of laundry baths quickly, and such builders only compete with the organic detergent and the soil for the free metal ions. The result is that while some of the free metal ions are removed from the solution, some ions do react with the organic detergent and the soil, thereby decreasing the detersive action. The use of the crystallization seed quickens the rate of precipitation of the metal hardness, thereby removing the hardness ions before they can adversely affect the detergency performance.

By using a material capable of forming a water-insoluble product with free metal ions in combination with a crystallization seed, the combined free metal ion concentration of an aqueous laundering liquor can be reduced to less than 0.5 grains of hardness within about 120 seconds. In fact, the preferred seeded builders can reduce the free metal hardness to less than 0.1 grains/gallon within about 30 seconds.

Preferred seeded builders consist of: a water-soluble material capable of forming a reaction product having a solubility in water of less than about $1.4 \times 10^{-2}$ wt.% (at 25° C) with divalent and polyvalent metal ions such as calcium, magnesium and iron; and a crystallization seed (0.001–20 micron diameter) which comprises a material which will not completely dissolve in water within 120 seconds at 25° C.

Specific examples of materials capable of forming the water-insoluble reaction product include the water-soluble salts of carbonates, bicarbonates, sesquicarbonates, silicates, aluminates and oxalates. The alkali metal, especially sodium, salts of the foregoing materials are preferred for convenience and economy.

The crystallization seed employed in such seeded builders is preferably selected from the group consisting of calcium carbonate; calcium and magnesium oxalates; barium sulfate; calcium, magnesium and aluminum silicates; calcium and magnesium oxides; calcium and magnesium salts of fatty acids having 12 to 22 carbon atoms; calcium and magnesium hydroxides; calcium fluoride; and barium carbonate. Specific examples of such seeded builder mixtures comprise: 3:1 wt. mixtures of sodium carbonate and calcium carbonate having a 5 micron particle diameter; 2.7:1 wt. mixtures of sodium sesquicarbonate and calcium carbonate having a particle diameter of 0.5 microns; 20:1 wt. mixtures of sodium sesquicarbonate and calcium hydroxide having a particle diameter of 0.01 micron; and a 3:3:1 wt. mixture of sodium carbonate sodium aluminate and calcium oxide having a particle diameter of 5 microns.

A seeded builder comprising a mixture of sodium carbonate and calcium carbonate is especially preferred herein. A highly preferred seeded builder comprises a 30:1 to 5:1 (wt. $Na_2CO_3:CaCO_3$) mixture of sodium carbonate and calcium carbonate wherein the calcium carbonate has an average particle diameter from 0.01 micron to 5 microns.

Another type of builder useful herein includes various substantially water-insoluble materials which are capable of reducing the hardness content of laundering liquors, e.g., by ion-exchange processes. Examples of such builder materials include the phosphorylated cloths disclosed in U.S. Pat. No. 3,424,545, to R. A. Bauman, issued Jan. 28, 1969, incorporated herein by reference.

The complex aluminosilicates, i.e., zeolite-type materials, are another type of substantially water-insoluble builder useful in the present compositions, and these materials readily soften water, i.e., remove $Ca^{++}$ hardness. Both the naturally occurring and synthetic "zeolites," especially the zeolite A and hydrated zeolite A materials, are useful for this builder/softener purpose. A description of zeolite A materials and a method of preparation appears in U.S. Pat. No. 2,882,243, entitled MOLECULAR SIEVE ADSORBENTS, issued Apr. 14, 1959, incorporated herein by reference.

Optional Ingredients

The compositions herein can contain all manner of detergent adjunct materials and carriers commonly found in laundering and cleaning compositions. For example, various perfumes, optical bleaches, fillers, anti-caking agents, fabric softeners and the like can be present to provide the usual benefits occasioned by the use of such materials in detergent compositions.

Perborate bleaches commonly employed in European detergent compositions can also be present as a component of the instant detergent compositions, and are added thereto as dry admixes.

Enzymes, especially the thermally stable proteolytic and lipolytic enzymes used in laundry detergents, can be dry-mixed in the compositions herein.

Materials such as sodium sulfate can be used as fillers for the granular compositions herein. Water and water-alcohol mixtures (especially 20:1 to 10:1 wt. water/ethanol mixtures) are useful carriers for liquid compositions comprising the TMO-based zwitterionic surfactants and builders disclosed herein.

It is to be understood that the use of builders in combination with the TMO-based zwitterionic surfactants herein provides enhanced detergency performance. These enhanced benefits arise by virtue of the water-softening action of the builder materials, as well as the increased alkalinity of laundering liquors containing preferred builders such as sodium tripolyphosphate and the inherent cleaning action of the builders, themselves (especially builder materials such as the phosphates). However, it has been experimentally determined that builders are particularly useful when employed in combination with TMO-based zwitterionics having from 1 to about 3 tetramethyleneoxide moieties in the molecule.

The advantages of the present compositions are more fully appreciated when it is recognized that "ordinary" anionic and nonionic surfactants, used in combination with non-phosphorus builders such as seeded carbonates, etc., do not give performance equivalent to that achieved with phosphate builders. However, the TMO-based zwitterionics herein, used in combination with non-phosphate builders, do exhibit detergency performance substantially equivalent to commercial, phosphate-built, anionic detergents.

The following examples illustrate the compositions of this invention but are not intended to be limiting thereof.

EXAMPLE I

A phosphate-built detergent composition according to the present invention is as follows:

| Ingredient | % (wt.) |
|---|---|
| Compound G* | 15 |
| Sodium tripolyphosphate | 35 |
| Sodium sulfate | 30 |
| Sodium silicate (water-soluble) | 15 |
| Water and minors | Balance |

*9-dimethyloctadecylammonio-5-oxanonane-1-sulfonate, Compound G as prepared hereinabove.

The composition of Example I is prepared by dissolving all ingredients in water to provide a substantially homogeneous crutcher mix. The crutcher mix is spray-dried in standard fashion to provide solid granules.

The composition of Example I (1 cup) is added to a standard top-loading automatic washing machine containing ca. 25 gallons of water. A load of mixed fabrics is laundered in the resulting liquor using the machine manufacturer's instructions. After rinsing and drying, the fabrics are found to be substantially free from heavy clay soil stains originally present thereon. The clay soil removal performance of the composition is fully equivalent to, or substantially better than, that of commercially available, built laundry detergents containing common anionic surfactants.

In the composition of Example I, Compound G is replaced by an equivalent amount of 19-dimethyloctadecylammonio-5,10,15-trioxanonadecane-1-sulfonate; 24-dimethyloctadecylammonio-5,10,15,20-tetraoxatetracosane-1-sulfonate; 19-dimethyloctadecylammonio-5,10,15-trioxanonadecane-1-sulfate; and 24-dimethyloctadecylammonio-5,10,15,20-tetraoxatetracosane-1-hydrogen phosphonate, respectively, and good detergency performance is secured.

In the composition of Example I, the sodium tripolyphosphate is replaced by an equivalent amount of a 20:1 (wt.) mixture of $Na_2CO_3$ and particulate $CaCO_3$ (avg. particle diameter 1 micron) and excellent detergency performance is secured.

EXAMPLE II

A highly-built detergent composition containing a proteolytic enzyme and especially adapted for use under European washing conditions is as follows.

| Ingredient | % (wt.) |
| --- | --- |
| Compound I* | 20 |
| Sodium tripolyphosphate | 50 |
| Enzyme** | 0.15 |
| Sodium sulfate | 25 |
| Water, perfume, dye and minors | |

*24-dimethyloctadecylammonio-5,10,15,20-tetraoxatetracosane-1-sulfonate, Compound I prepared hereinabove.
**Proteolytic enzyme from *Thermoactinomyces vulgaris* ATCC15734.

The composition of Example II is prepared in the same manner as the composition of Example I, with the exception that the enzyme is not passed through the crutcher mix or spray-drying tower, but is added to the detergent granules after spray-drying is complete in order to maintain enzyme activity.

The composition of Example II is used in a front-loading washing machine typical of that used in Germany. The composition is used at a concentration of ca. 250 ppm of the laundering liquor. Cleaning of fabrics heavily soiled with clay is equivalent to, or substantially better than, that secured with well-known commercial detergents.

The composition of Example II is exceptionally useful as a laundry pre-soak to assist in the removal of clay, lipid and proteinaceous (e.g., blood stains) soils from fabrics.

EXAMPLE III

A non-phosphate built detergent composition according to the present invention is as follows:

| Ingredient | % (wt.) |
| --- | --- |
| Compound G + I* | 15 |
| Trisodium nitrilotriacetate | 20 |
| Sodium sulfate | 45 |
| Sodium silicate (water-soluble) | 10 |
| Water and minors | Balance |

*1:1 wt. mixture of Compounds G and I, as prepared hereinabove.

The composition of Example III is prepared by dissolving all ingredients in water to provide a substantially homogeneous crutcher mix. The crutcher mix is spray-dried in standard fashion to provide solid granules.

| Ingredient | % (wt.) |
| --- | --- |
| Compound G + I* | 15 |
| Trisodium nitrilotriacetate | 20 |
| Sodium sulfate | 45 |
| Sodium silicate (water-soluble) | 10 |
| Water and minors | Balance |

*1:1 wt. mixture of Compounds G and I, as prepared hereinabove.

The composition of Example III (1 cup) is used to launder a mixed load of cotton, polyester and polyester/cotton blend fabrics stained with clay and oily soils in a standard top-loading automatic washing machine according to manufacturer's instructions. After rinsing and drying, the fabrics are found to be substantially free from both the clay and the oily stains originally present thereon. The detergency performance of the composition is fully equivalent to, or substantially better than, that of commercially available, low-phosphate built laundry detergents containing common anionic surfactants.

In the composition of Example III, the nitrilotriacetate builder is replaced by an equivalent amount of mellitic acid, oxydisuccinic acid, citric acid, and ethylenediaminetetraacetic acid, respectively, and superior detergency performance is secured.

In the composition of Example III, the water-soluble nitrilotriacetate builder is replaced by an equivalent amount of hydrated zeolite A (avg. particle diameter ca. 1 micron) and superior detergency performance is secured.

In the composition of Example III, the mixture of Compounds G and I is replaced by an equivalent amount of 19-dimethyloctadecylammonio-5,10,15-trioxanonadecane-1-sulfate, 24-dimethyloctadecylammonio-5,10,15,20-tetraoxatetracosane-1-hydrogen phosphonate, and the 5-oxanonane-1-sulfonate derivatives (corresponding to Compound G) of decyldimethylamine, dodecyldimethylamine, tetradecyldimethylamine, hexadecyldimethylamine, trioctylamine and bis-(decyl)methylamine, respectively, and excellent detergency performance, especially on clay soils, is secured.

EXAMPLE IV

A built liquid detergent composition is as follows:

| Ingredient | % (wt.) |
| --- | --- |
| Compound H* | 20 |
| Sodium citrate | 15 |
| Sodium nitrilotriacetate | 5 |
| Triethanolamine | 1 |
| Aqueous ethanol (90:10 water-ethanol) | |

*19-dimethyloctadecylammonio-5,10,15-trioxanonadecane-1-sulfonate, Compound H prepared hereinabove.

The composition of Example IV is prepared by dissolving all components in the aqueous ethanol to provide a homogeneous solution.

The composition of Example IV is particularly desirable as a spot-cleaning composition which is directly applied to heavily soiled fabrics prior to their laundering in an automatic washing machine. In use, ca. 0.25 cup of the composition of Example IV is dispensed and portions are poured directly onto heavily soiled areas of fabrics to be laundered. The soiled areas are rubbed briefly to work the composition into the fabric, and the fabrics are thereafter placed in a standard top-loading automatic washing machine. The fabrics are thereafter laundered in standard fashion, rinsed and dried. Fabrics treated in this manner are found to be substantially free from heavy clay and oily soils.

What is claimed is:
1. A detergent composition, consisting essentially of:
   a. from about 1% to about 99% by weight of a water-soluble surfactant of the formula:

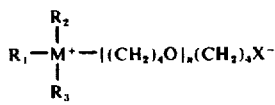

wherein $R_1$, $R_2$ and $R_3$ are independently selected from $C_1$ to $C_{30}$ alkyl or alkenyl moieties, aryl moieties, alkaryl moieties having an alkyl group in the range of $C_1$ to $C_{30}$, or wherein two R groups are joined to form a $C_4$ to $C_6$ heteroring with M; M is nitrogen or phosphorus; $n$ is an integer from 1 to about 20; and X is a water-solubilizing anionic moiety; and
   b. from about 5% to about 95% by weight of a detergency builder.

2. A composition according to claim 1 wherein the water-soluble surfactant represents from about 6% to about 50% by weight of the composition and the detergency builder represents from about 15% to about 65% by weight of the composition.

3. A composition according to claim 1 wherein X is sulfate or sulfonate.

4. A composition according to claim 1 wherein $R_1 + R_2 + R_3$, together, contain at least about 12 carbon atoms.

5. A composition according to claim 4 wherein $R_1$ is a straight chain or branched chain $C_{10}$–$C_{30}$ alkyl or alkenyl moiety, or an alkaryl moiety having $C_6$–$C_{24}$ alkyl group, and wherein $R_2$ and $R_3$ are each independently selected from $C_1$–$C_4$ alkyl or alkenyl moieties or hydroxy-substituted $C_1$–$C_4$ alkyl or alkenyl moieties.

6. A composition according to claim 5 wherein $R_1$ is a $C_{14}$–$C_{22}$ alkyl moiety or alkaryl moiety having a $C_8$–$C_{16}$ alkyl group, $R_2$ and $R_3$ are each methyl, X is sulfate or sulfonate, M is nitrogen, and $n$ is an integer in the range from 1 to about 10.

7. A composition according to claim 6 wherein the surfactant is selected from 9-dimethyloctadecylammonio-5-oxanonane-1-sulfonate, 19-dimethyloctadecylammonio-5,10,15-trioxanonadecane-1-sulfonate, 24-dimethyloctadecylammonio-5,10,15,20-tetraoxatetracosane-1-sulfonate, 19-dimethyloctadecylammonio-5,10,15-trioxanonadecane-1-sulfate, or mixtures thereof.

8. A composition according to claim 4 wherein $R_1$ and $R_2$ are each independently selected from $C_6$–$C_{22}$ alkyl or alkenyl moieties or alkaryl moieties having a $C_6$–$C_{16}$ alkyl group and wherein $R_3$ is a $C_1$–$C_4$ alkyl or alkenyl moiety or hydroxy-substituted $C_1$–$C_4$ alkyl or alkenyl moiety.

9. A composition according to claim 8 wherein $R_1$ and $R_2$ are each selected from $C_8$–$C_{16}$ alkyl moieties, $R_3$ is methyl, X is sulfate or sulfonate, M is nitrogen, and $n$ is an integer in the range from 1 to about 10.

10. A composition according to claim 4 wherein $R_1$, $R_2$ and $R_3$ are each independently selected from $C_6$–$C_{16}$ alkyl or alkenyl moieties or alkaryl moieties having a $C_6$–$C_{10}$ alkyl group.

11. A composition according to claim 10 wherein $R_1$, $R_2$ and $R_3$ are each independently selected from $C_8$–$C_{16}$ alkyl moieties, the sum of $R_1 + R_2 + R_3$ carbon atoms being in the range from about 24 to about 48, X is sulfate or sulfonate, M is nitrogen, and $n$ is an integer in the range from 1 to about 10.

12. A composition according to claim 1 wherein there is present from about 15% to about 65% by weight of a water-soluble detergency builder.

13. A composition according to claim 12 wherein the builder is an inorganic detergency builder.

14. A composition according to claim 13 wherein the inorganic builder is sodium tripolyphosphate.

15. A composition according to claim 12 wherein the builder is an organic detergency builder.

16. A composition according to claim 15 wherein the organic builder is sodium nitrilotriacetate.

17. A composition according to claim 1 wherein the detergency builder is a seeded builder.

18. A composition according to claim 17 wherein the seeded builder comprises a 30:1 to 5:1 weight mixture of sodium carbonate and particulate calcium carbonate having an average particle diameter from 0.01 microns to 5 microns.

19. A composition according to claim 1 wherein the detergency builder is substantially water-insoluble.

20. A composition according to claim 19 wherein the detergency builder is a zeolite-type material.

* * * * *

UNITED STATES PATENT OFFICE
CERTIFICATE OF CORRECTION

Patent No. 4,000,091  Dated December 28, 1976

Inventor(s) George Edward Wentler

It is certified that error appears in the above-identified patent and that said Letters Patent are hereby corrected as shown below:

Column 3, line 66, "$R_a$" should read -- $R_1$ --. Column 4, line 66, "tetiary" should read -- tertiary --. Column 5, line 26, formula should appear as follows -- $HO(CH_2)_4O(CH_2)_4O(CH_2)_4O(CH_2)_4OH$ --. Column 6, line 64, "Trioxanonadecylene-" should read -- Trioxanonadecylene)- --. Column 7, line 25, "0.04" should read -- 0.40 --; line 30, "$Na_2SO_4$" should read -- $Na_2SO_4$ --; line 39, "$n-C_{10}H_{21}(CH_3)_2N$" should read -- $n-C_{10}H_{21}(CH_3)_2N$ --; line 40, "$n-C_{12}H_{25}(CH_3)_2N$" should read -- $n-C_{12}H_{25}(CH_3)_2N$ --; line 40, "$n-C_{14}H_{29}(CH_3)_2N$" should read -- $n-C_{14}H_{29}(CH_3)_2N$ --; line 40, "$n-C_{16}H_{33}(CH_3)_2N$" should read -- $n-C_{16}H_{33}(CH_3)_2N$ --; line 43, "$n-C_{12}$" should read -- $n-C_{12}$ --. Column 8, line 19, "dicotylmethylamine" should read -- dioctylmethylamine --; line 27, "-1Sulfate" should read -- -1-Sulfate --; line 47, "colled" should read -- cooled --; line 66, "Phosphate" should read -- Phosphonate --. Column 9, line 41, "phosphates" should read -- phosphate --; line 48, "triphsophonic" should read -- triphosphonic --;

UNITED STATES PATENT OFFICE
CERTIFICATE OF CORRECTION

Patent No. 4,000,091  Dated December 28, 1976

Inventor(s) George Edward Wentler

It is certified that error appears in the above-identified patent and that said Letters Patent are hereby corrected as shown below:

Column 10, line 65, "grains/-" should read -- grains/ --. Column 11, line 28, "carbonate sodium" should read -- carbonate, sodium --. Column 13, line 27, after "Water, perfume, dye and minors" insert -- Balance --. Column 14, lines 1-9, delete the table; line 55, after "ethanol)" insert -- Balance --.

Signed and Sealed this

Tenth Day of January 1978

[SEAL]

Attest:

RUTH C. MASON
Attesting Officer

LUTRELLE F. PARKER
Acting Commissioner of Patents and Trademarks